US009526831B2

(12) United States Patent
Kondoh et al.

(10) Patent No.: US 9,526,831 B2
(45) Date of Patent: Dec. 27, 2016

(54) PHARMACEUTICAL INJECTION DEVICE

(75) Inventors: Tsuguhiro Kondoh, Ehime (JP); Seiji Kikuchi, Ehime (JP); Takashi Hanada, Hyogo (JP)

(73) Assignees: PANASONIC HEALTHCARE CO., LTD., Ehime (JP); JCR PHARMACEUTICALS CO., LTD., Hyogo (JP)

( * ) Notice: Subject to any disclaimer, the term of this patent is extended or adjusted under 35 U.S.C. 154(b) by 413 days.

(21) Appl. No.: 14/343,493

(22) PCT Filed: Sep. 10, 2012

(86) PCT No.: PCT/JP2012/005710
§ 371 (c)(1),
(2), (4) Date: Mar. 7, 2014

(87) PCT Pub. No.: WO2013/038639
PCT Pub. Date: Mar. 21, 2013

(65) Prior Publication Data
US 2014/0228763 A1    Aug. 14, 2014

(30) Foreign Application Priority Data

Sep. 12, 2011    (JP) .................................. 2011-198101

(51) Int. Cl.
*A61M 5/172*    (2006.01)
*A61M 5/20*    (2006.01)
(Continued)

(52) U.S. Cl.
CPC ........... *A61M 5/172* (2013.01); *A61M 5/1452* (2013.01); *A61M 5/20* (2013.01); *A61M 5/2066* (2013.01);
(Continued)

(58) Field of Classification Search
CPC   A61M 5/172; A61M 5/2066; A61M 5/31568; A61M 5/1452; A61M 5/20; A61M 2205/59; A61M 2205/215; A61M 2205/50; A61M 2205/502; A61M 2005/206; A61M 5/31546; A61M 2005/31588; A61M 2205/14; A61M 5/31576; A61M 5/14566; A61M 5/31593; A61M 5/1684; A61M 5/326; A61M 2005/3125; A61M 2005/14573; A61M 2205/3606

See application file for complete search history.

(56) References Cited

U.S. PATENT DOCUMENTS 6,585,698 B1    7/2003    Packman et al.
6,869,413 B2    3/2005    Langley et al.
(Continued)

FOREIGN PATENT DOCUMENTS

JP    11-137845 A    5/1999
JP    2003-309825 A    10/2003
(Continued)

OTHER PUBLICATIONS

International Search Report for PCT/JP2012/005710 dated Oct. 23, 2012.
(Continued)

*Primary Examiner* — Kevin C Sirmons
*Assistant Examiner* — Amber Stiles
(74) *Attorney, Agent, or Firm* — Pearne & Gordon LLP

(57) ABSTRACT

This pharmaceutical injection device comprises a main body case (2) that has an injection needle insertion and retraction opening (1); pharmaceutical syringe mounting portion (3) that is provided within the main body case (2); a piston (5) that is provided movably with respect to a pharmaceutical syringe (4) that is mounted to the pharmaceutical syringe
(Continued)

mounting portion (3); a drive mechanism (6) that drives the piston (5); a controller (7) that is electrically connected to the drive mechanism (6); and a display section (35) that is electrically connected to the controller (7). The controller (7) updates the display content that is displayed on the display section (35) according to the number of times the drive mechanism (6) has been driven, and saves this updated display content in a memory (51), so that when the drive mechanism (6) has been driven a specific number of times, the display contents during the various instances of drive that were saved in the memory (51) are combined.

8 Claims, 13 Drawing Sheets

(51) Int. Cl.
- *A61M 5/145* (2006.01)
- *A61M 5/24* (2006.01)
- *G06F 19/00* (2011.01)
- *A61M 5/31* (2006.01)
- *A61M 5/315* (2006.01)

(52) U.S. Cl.
CPC ........ *A61M 5/31568* (2013.01); *A61M 5/2448* (2013.01); *A61M 5/31546* (2013.01); *A61M 2005/206* (2013.01); *A61M 2005/3125* (2013.01); *A61M 2005/31588* (2013.01); *A61M 2205/14* (2013.01); *A61M 2205/215* (2013.01); *A61M 2205/50* (2013.01); *A61M 2205/502* (2013.01); *A61M 2205/52* (2013.01); *A61M 2205/59* (2013.01); *G06F 19/3468* (2013.01)

(56) References Cited

U.S. PATENT DOCUMENTS

| | | |
|---|---|---|
| 6,942,646 B2 | 9/2005 | Langley et al. |
| 6,949,082 B2 | 9/2005 | Langley et al. |
| 6,969,370 B2 | 11/2005 | Langley et al. |
| 6,997,906 B2 | 2/2006 | Langley et al. |
| 7,052,484 B2 | 5/2006 | Veasey et al. |
| 7,081,108 B2 | 7/2006 | Langley et al. |
| 7,699,815 B2 | 4/2010 | Langley et al. |
| 8,128,603 B2 | 3/2012 | Langley et al. |
| 8,469,922 B2 | 6/2013 | Langley et al. |
| 2004/0002436 A1 | 1/2004 | Grimm et al. |
| 2004/0003029 A1 | 1/2004 | Islam et al. |
| 2004/0004431 A1 | 1/2004 | Nishikawa |
| 2004/0004915 A1 | 1/2004 | Uchiyama |
| 2004/0005431 A1 | 1/2004 | Moulin et al. |
| 2004/0005432 A1 | 1/2004 | Ridout et al. |
| 2004/0007317 A1 | 1/2004 | Wu |
| 2004/0007800 A1 | 1/2004 | Lin et al. |
| 2004/0009787 A1 | 1/2004 | Oh et al. |
| 2004/0012235 A1 | 1/2004 | Freller |
| 2004/0024364 A1 | 2/2004 | Langley et al. |
| 2004/0030296 A1 | 2/2004 | Langley et al. |
| 2004/0030298 A1 | 2/2004 | Veasey et al. |
| 2004/0044317 A1 | 3/2004 | Langley et al. |
| 2004/0049156 A1 | 3/2004 | Langley et al. |
| 2004/0054318 A1 | 3/2004 | Langley et al. |
| 2004/0054319 A1 | 3/2004 | Langley et al. |
| 2004/0054328 A1 | 3/2004 | Langley et al. |
| 2004/0054329 A1 | 3/2004 | Langley et al. |
| 2004/0073173 A1 | 4/2004 | Langley et al. |
| 2004/0078001 A1 | 4/2004 | Langley et al. |
| 2004/0097873 A1 | 5/2004 | Langley et al. |
| 2004/0122355 A1 | 6/2004 | Langley et al. |
| 2007/0187899 A1 | 8/2007 | Bush et al. |
| 2008/0294094 A1* | 11/2008 | Mhatre ............... A61M 5/1413 604/65 |
| 2010/0261987 A1* | 10/2010 | Kamath ............. A61B 5/14532 600/365 |
| 2011/0025760 A1 | 2/2011 | Rosati et al. |
| 2011/0257602 A1 | 10/2011 | Watanabe et al. |
| 2012/0032317 A1 | 2/2012 | Cruz |
| 2012/0323176 A1 | 12/2012 | Watanabe et al. |

FOREIGN PATENT DOCUMENTS

| | | |
|---|---|---|
| JP | 2004-06-03 A | 6/2004 |
| JP | 2004-516107 A | 6/2004 |
| WO | 2010073452 A1 | 1/2010 |
| WO | 2010073452 A1 | 7/2010 |
| WO | 2011108225 A1 | 9/2011 |

OTHER PUBLICATIONS

Extended European Search Report for Application No. 12831039.8 dated Jan. 19, 2015.

Notice of Allowance for Japanese Patent Application No. 2013-533488 dated Jun. 2, 2015.

* cited by examiner

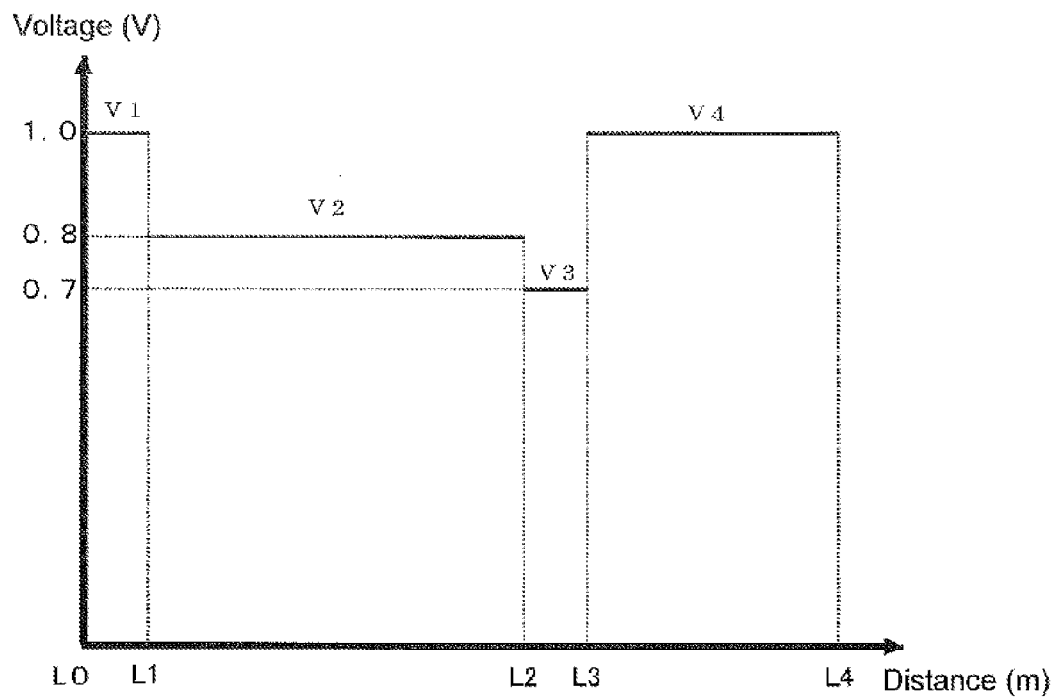

L0: initial position of separation gasket rear end
L1: position when separation gasket rear end touches bypass
(at start of mixing operation)
L2: position when separation gasket rear end touches push-in gasket
(at end of mixing operation)
L3: position of separation gasket rear end after completion of air venting operation
L4: position of separation gasket rear end after completion of pharmaceutical injection operation

FIG. 8

L0 (initial position)

L1 (before mixing operation)
L0 (initial position)

L3 (at completion of air venting operation)
L2 (at completion of mixing operation)
L1 (at start of mixing operation)
L0 (initial position)

L4 (at completion of pharmaceutical injection operation)
L3 (at completion of air venting operation)
L2 (at completion of mixing operation)
L1 (at start of mixing operation)
L0 (initial position)

PHARMACEUTICAL INJECTION DEVICE

TECHNICAL FIELD

The present invention relates to a pharmaceutical injection device.

BACKGROUND ART

A conventional pharmaceutical injection device comprised a main body case that had an injection needle insertion and retraction opening, a pharmaceutical syringe mounting portion provided within this main body case, a piston provided movably with respect to a pharmaceutical syringe that was mounted to this pharmaceutical syringe mounting portion, a drive mechanism for driving this piston, a controller that was electrically connected to this drive mechanism, and a display section that was electrically connected to this controller (see Patent Literature 1, for example).

CITATION LIST

Patent Literature

Patent Literature 1: Japanese Unexamined Patent Application Publication (Translation of PCT Application) No. 2004-516107

SUMMARY

However, the following problems were encountered with the conventional pharmaceutical injection device discussed above.

Specifically, with the pharmaceutical injection device disclosed in the above-mentioned publication, after a pharmaceutical syringe has been mounted to the pharmaceutical syringe mounting portion provided within the main body case, the patient presses a pharmaceutical injection button, whereupon the drive mechanism drives the piston, and a specific amount of the pharmaceutical inside the pharmaceutical syringe is injected into the patient.

In other words, with this type of pharmaceutical injection device, the patient himself is the one to inject the pharmaceutical into his own body by operating the device, and such devices are often used in injecting a growth hormone into a child. To continue the description while referring to this example, when a pharmaceutical injection device such as this is used, even a child can easily inject the proper dose of growth hormone all by himself.

Nevertheless, although we have said that the user can 'easily inject' the pharmaceutical, he still has to insert an injection needle into his body, and children in particular dislike this, which means that there is the risk that the user will not perform the pharmaceutical injections as scheduled. As a result, the therapeutic effect may be diminished.

In view of this, it is an object of the present invention to provide a pharmaceutical injection device with which the therapeutic effect can be enhanced.

To achieve the stated object, the present invention comprises a main body case, a pharmaceutical syringe mounting portion, a piston, a drive mechanism, a controller, and a display section. The main body case has an injection needle insertion and retraction opening. The pharmaceutical syringe mounting portion is provided within the main body case. The piston is provided movably with respect to a pharmaceutical syringe that is mounted to the pharmaceutical syringe mounting portion. The drive mechanism drives the piston. The controller is electrically connected to the drive mechanism. The display section is electrically connected to the controller. The controller updates the display content that is displayed on the display section according to the number of times the drive mechanism has been driven, and saves the updated display content in a memory, so that when the number of times the drive mechanism has been driven reaches a specific number, the display contents during the various instances of drive that were saved in the memory are combined.

ADVANTAGEOUS EFFECTS

With the pharmaceutical injection device pertaining to the present invention, the controller updates the display content that is displayed on the display section according to the number of times the drive mechanism has been driven, and saves the updated display content in a memory. Then, when the drive mechanism has been driven a specific number of times, the controller combines at least a plurality of the display contents during the various instances that were saved in the memory. Consequently, the display content is updated every time the pharmaceutical is injected, and when the number of times the drive mechanism has been driven reaches a specific number of times, at least a plurality of the display contents during the various instances saved in the memory are combined, and a finished product display is given.

Accordingly, even a child, for example, can actually enjoy performing the pharmaceutical injections as scheduled, and as a result the therapeutic effect can be enhanced.

BRIEF DESCRIPTION OF DRAWINGS

FIG. 8 is a graph of the operating state during mixing in the pharmaceutical injection device in FIG. 1;

DESCRIPTION OF EMBODIMENTS

Embodiments of the present invention will now be described through reference to the appended drawings.

Embodiment 1

Figure 1:
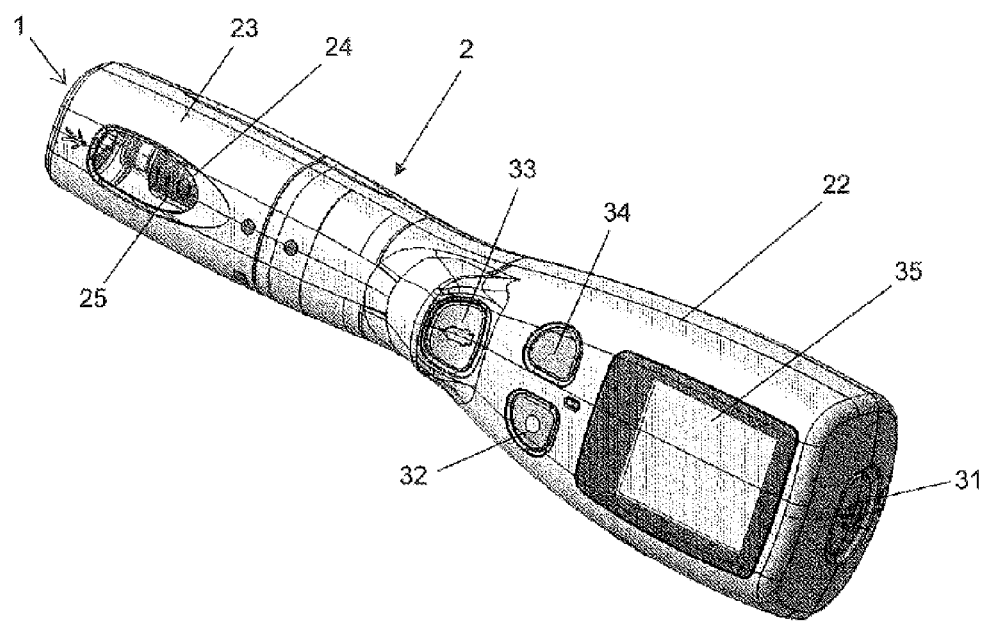
FIG. 1 is an oblique view of the pharmaceutical injection device pertaining to an embodiment of the present invention.
Figure 2:
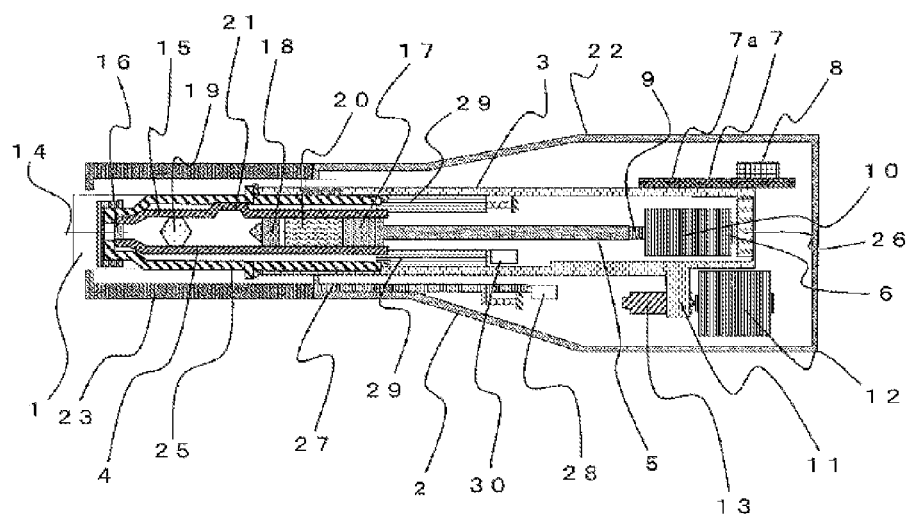
FIG. 2 is a cross section of the pharmaceutical injection device in FIG. 1.

As shown in FIGS. 1 and 2, the pharmaceutical injection device in this embodiment comprises a substantially cylindrical main body case 2, a pharmaceutical syringe mounting portion 3, a pharmaceutical syringe 4, a piston 5, a drive mechanism 6, a controller 7, and an orientation sensor 8. The main body case 2 has an injection needle insertion and retraction opening 1 on its distal end side. The pharmaceutical syringe mounting portion 3 is provided within the main body case 2. The pharmaceutical syringe 4 is mounted within the pharmaceutical syringe mounting portion 3. The piston 5 is provided movably with respect to the pharmaceutical syringe 4. The drive mechanism 6 drives the piston 5. The controller 7 is electrically connected to the drive mechanism 6. The orientation sensor 8 is electrically connected to the controller 7.

The orientation sensor 8 is mounted on a substrate 7a having the controller 7. The substrate 7a is installed so as to be parallel to the drive direction of the piston 5.

The drive mechanism 6 is made up of a bolt 9 inserted into a rear end opening in the piston 5, and a piston drive motor 10 for driving the bolt 9. Specifically, when the piston drive motor 10 is rotated in one direction, the bolt 9 pushes the piston 5 toward the injection needle insertion and retraction opening 1. Conversely, and when the piston drive motor 10 is rotated in the other direction, the piston 5 is pulled back toward the piston drive motor 10.

The piston drive motor 10 and the piston 5 are disposed along with the pharmaceutical syringe 4 inside the pharmaceutical syringe mounting portion 3. Female threads 11 are provided toward the outside of the rear end side of the pharmaceutical syringe mounting portion 3. A bolt 13 of a needle insertion and retraction drive motor 12 meshes with these female threads 11. That is, when the needle insertion and retraction drive motor 12 is driven, the female threads 11 and the bolt 13 mesh, causing the pharmaceutical syringe mounting portion 3 to move back and forth with respect to the injection needle insertion and retraction opening 1. This causes an injection needle 14 provided on the distal end side of the pharmaceutical syringe 4 to come out of the injection needle insertion and retraction opening 1.

Figure 9A:
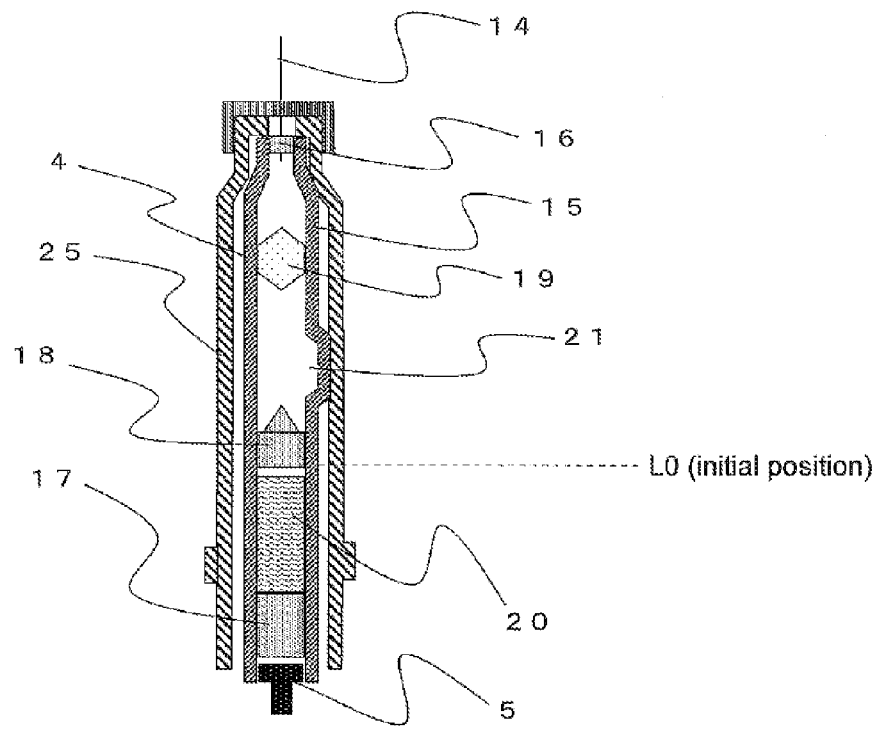
FIG. 9A is a cross section of the operating state during mixing in the pharmaceutical injection device pertaining in FIG. 1.

As shown in FIG. 9A, the pharmaceutical syringe 4 has a cylinder 15, a distal end gasket 16, a push-in gasket 17, a separation gasket 18, a solid pharmaceutical 19, a liquid pharmaceutical 20, and a bypass 21. The distal end gasket 16 is provided on the distal end side within the cylinder 15. The push-in gasket 17 is provided on the rear end side within the cylinder 15. The separation gasket 18 is provided in the middle within the cylinder 15. The solid pharmaceutical 19 is contained inside the cylinder 15 between the distal end gasket 16 and the separation gasket 18. The liquid pharmaceutical 20 is contained inside the cylinder 15 between the push-in gasket 17 and the separation gasket 18. The bypass 21 protrudes in the outer peripheral direction of the cylinder 15 at the portion of the cylinder 15 between the distal end gasket 16 and the separation gasket 18.

The controller 7 actuates the drive mechanism 6 so that the push-in gasket 17 is pressed by the piston 5 to the distal end gasket 16 side after orientation and position sensing by the orientation sensor 8.

Also, the rate at which the push-in gasket 17 is pushed in by the piston 5 is set so that if we let V1 be the push-in rate when the separation gasket 18 reaches the bypass 21, V2 be the push-in rate at the point when the separation gasket 18 goes through the bypass 21, V3 be the push-in rate at the point when air is vented after the separation gasket 18 has gone through the bypass 21, and V4 be the push-in rate at the point when a pharmaceutical is injected after air venting, the push-in rate V2 will be lower than the push-in rate V1.

Returning to FIGS. 1 and 2, the main body case 2 is made up of a housing 22 and a distal end cap 23 on the distal end side of the housing 22. The distal end cap 23 is removably attached to the housing 22, and a window 24 is provided on the outer peripheral part of the distal end cap 23.

After the pharmaceutical syringe 4 has been mounted inside the pharmaceutical syringe mounting portion 3, the outer periphery of the pharmaceutical syringe 4 is covered by a syringe cover 25 (see FIG. 9A, etc.), and in this state, the injection needle 14 is mounted to the distal end gasket 16 on the distal end side of the pharmaceutical syringe 4.

When the piston 5 pushes the push-in gasket 17 forward, the liquid pharmaceutical 20 goes through the bypass 21 and flows to the solid pharmaceutical 19 side, and when the push-in gasket 17 moves farther forward, the liquid pharmaceutical 20 flows out of the injection needle 14.

The rotation of the piston drive motor 10 is detected by an encoder 26. Consequently, the amount by which the piston 5 protrudes (moves) is sensed. The solid pharmaceutical 19 and the liquid pharmaceutical 20 contained inside the pharmaceutical syringe 4 are put in at a pharmaceutical company, etc.

The housing 22 of the main body case 2 also houses a number of switches. More specifically, a distal end cap detector switch 28 is disposed at the rear end of a control rod 27 provided around the outer periphery of the pharmaceutical syringe mounting portion 3, on the distal end side of the housing 22. When the distal end cap 23 is mounted to the distal end of the housing 22, the control rod 27 is pushed rearward, and the distal end cap detector switch 28 detects that the distal end cap 23 has been mounted.

A control rod 29 is disposed inside the pharmaceutical syringe mounting portion 3. When the control rod 29 is pushed rearward by the syringe cover 25, a syringe cover detector switch 30 detects that the syringe cover 25 has been mounted.

The orientation sensor 8 is mounted on the substrate 7a having the controller 7. Since the substrate 7a is installed so as to be parallel to the drive direction of the piston 5, the orientation sensor 8 can properly sense acceleration with respect to the main body case 2. In this embodiment, the substrate 7a is installed parallel to the drive direction of the piston 5, but may instead be installed perpendicular to the drive direction of the piston 5.

Returning to FIG. 1, various control buttons and so forth are provided to the outer periphery of the housing 22 of the main body case 2. More specifically, a power button 31 is provided to the rear end of the housing 22. A mix button 32, a pharmaceutical injection button 33, an end button 34, and a display section 35 are provided to the outer periphery of the housing 22.

Figure 3:
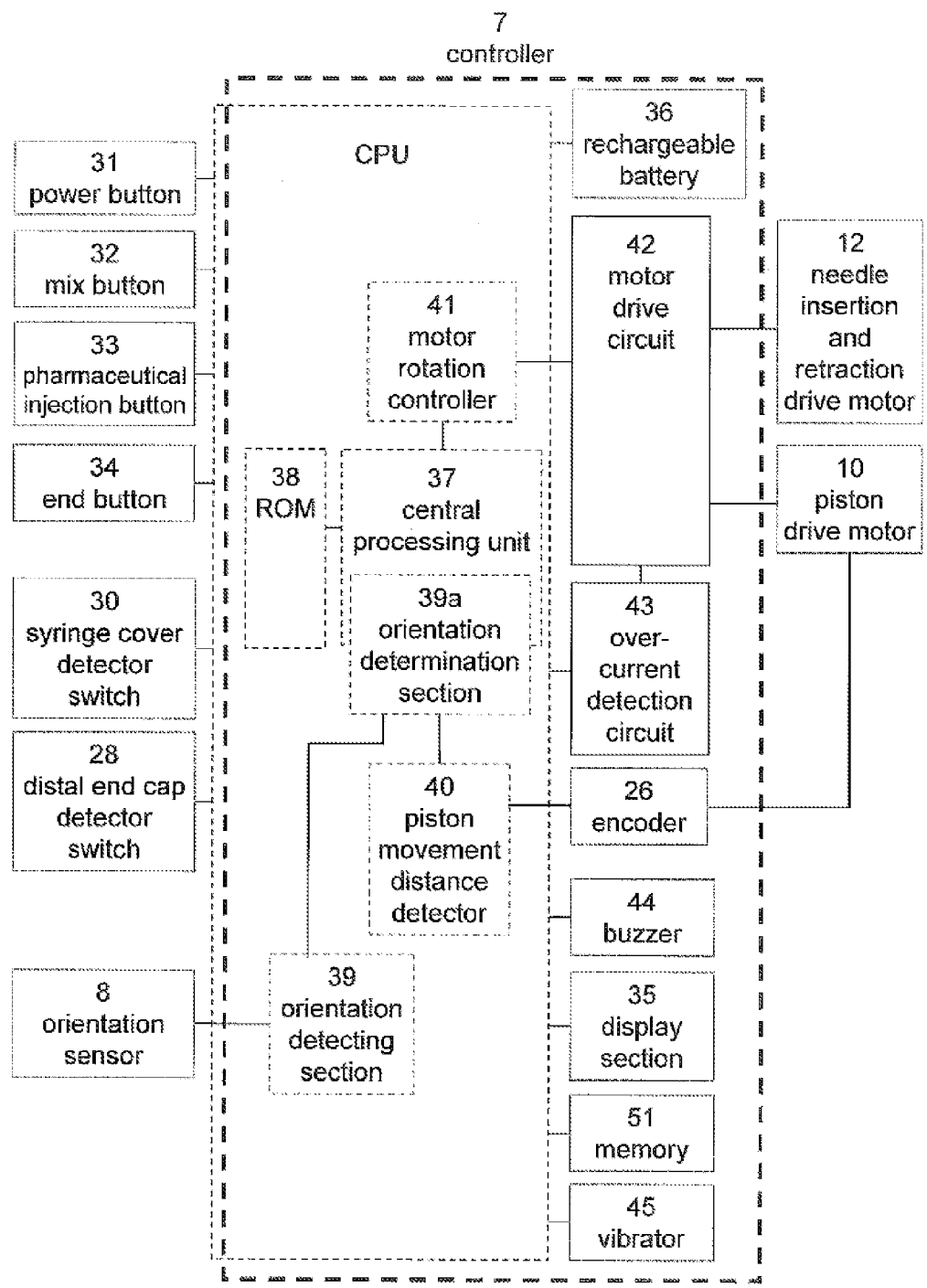
FIG. 3 is a control block diagram of the simplified electrical configuration of the pharmaceutical injection device in FIG. 1.

FIG. 3 is an electrical block diagram of the pharmaceutical injection device in FIG. 1.

The controller 7 is constituted by a microprocessor. As shown in FIG. 3, a rechargeable battery 36 is connected to the controller 7 and other electrically driven parts. The electrical connection state of the rechargeable battery 36 and the other electrically driven parts is not shown, to keep FIG. 3 from being too complicated.

A central processing unit 37 is provided inside the controller 7. The central processing unit 37 performs operational control over the various blocks shown in FIG. 3. A program that performs this operational control is written into a ROM 38. An orientation detecting section 39, a piston movement distance sensor 40, and a motor rotation controller 41 are connected to the central processing unit 37.

An orientation determination section 39*a* and the orientation sensor 8 are connected to the orientation detecting section 39. The orientation detecting section 39 converts the orientation sensing result from the orientation sensor 8 into information for determining the orientation at the orientation determination section 39*a*.

The orientation determination section 39*a* performs various kinds of operational control according to the orientation, such as using the orientation information obtained from the orientation detecting section 39 to compare the inclination sensed by the orientation sensor 8 with a set value, determine whether or not to drive the piston drive motor 10, etc.

The piston movement distance detector 40 is connected to the encoder 26. The encoder 26 is attached to the piston drive motor 10, which allows the movement distance of the piston 5 to be detected by detecting the rotation of the piston drive motor 10.

The motor rotation controller 41 is connected to a motor drive circuit 42. When the value detected by the piston movement distance detector 40 reaches a preset value, the motor rotation controller 41 controls the motor drive circuit 42 to change the movement speed of the piston 5.

The piston drive motor 10 and the needle insertion and retraction drive motor 12 are connected to the motor drive circuit 42. The motor drive circuit 42 is connected to an over-current detection circuit 43.

The motor drive circuit 42 is controlled by the motor rotation controller 41 while driving the piston drive motor 10 and the needle insertion and retraction drive motor 12.

The over-current detection circuit 43 is a circuit that detects the amount of current from the motor drive circuit 42, and detects malfunction of the motors.

The controller 7 is also connected to a buzzer 44 and a vibrator 45 for issuing a warning so as to alert the user to the current usage status of the device.

The controller 7 is also connected to the display section 35, which displays warnings and information for operating the device, and to a memory 51 for recording various kinds of data.

The above configuration will now be described through reference to the operational flowchart shown in FIG. 4.

Figure 4:
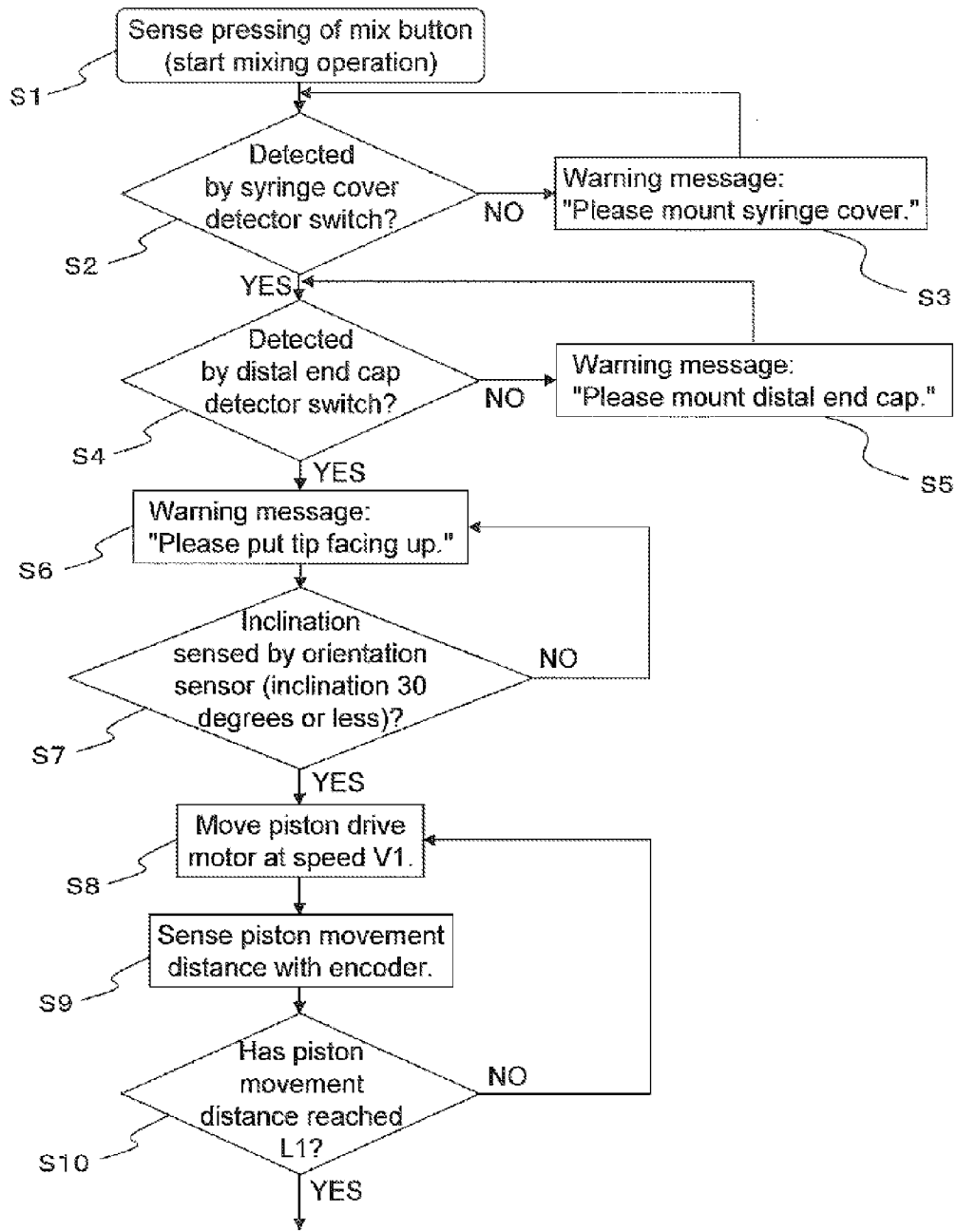
FIG. 4 is a flowchart of the operational control of the pharmaceutical injection device in FIG. 1.

First, as shown in FIG. 4, in S1 the mix button 32 is pressed (see FIG. 1). Then, in S2 the syringe cover detector switch 30 detects whether or not the syringe cover 25 has been mounted. If the syringe cover 25 has not been mounted, as shown in S3, a warning display of "Please mount syringe cover" is given on the display section 35 (see FIG. 1).

Once the mounting of the syringe cover 25 has been confirmed, the distal end cap detector switch 28 checks whether or not the distal end cap 23 has been mounted, as shown in S4. Here again, as shown in S5, if the distal end cap 23 has not been mounted, a warning display of "Please mount distal end cap" is given on the display section 35.

The following operation is not performed if the syringe cover 25 and the distal end cap 23 have not been mounted as shown in S2 and S4.

In S2 and S4, once it has been confirmed that the syringe cover 25 and the distal end cap 23 have been mounted, a display of "Please put tip facing up" is left on the display section 35 for a specific length of time.

In S7, the inclination of the pharmaceutical injection device is sensed by the orientation sensor 8. Hereinafter, the inclination will be referred to by using the direction perpendicular to the horizontal plane as zero degrees. If the inclination exceeds a specific value (the set value), the operation is halted until the inclination falls back to within the specific value (the set value), and operation is restarted once the inclination has been within the specific value for a specific length of time. When leakage from the injection needle is taken into account, it is preferable for the inclination at which operation is performed to be 30 degrees or less.

Figure 7:
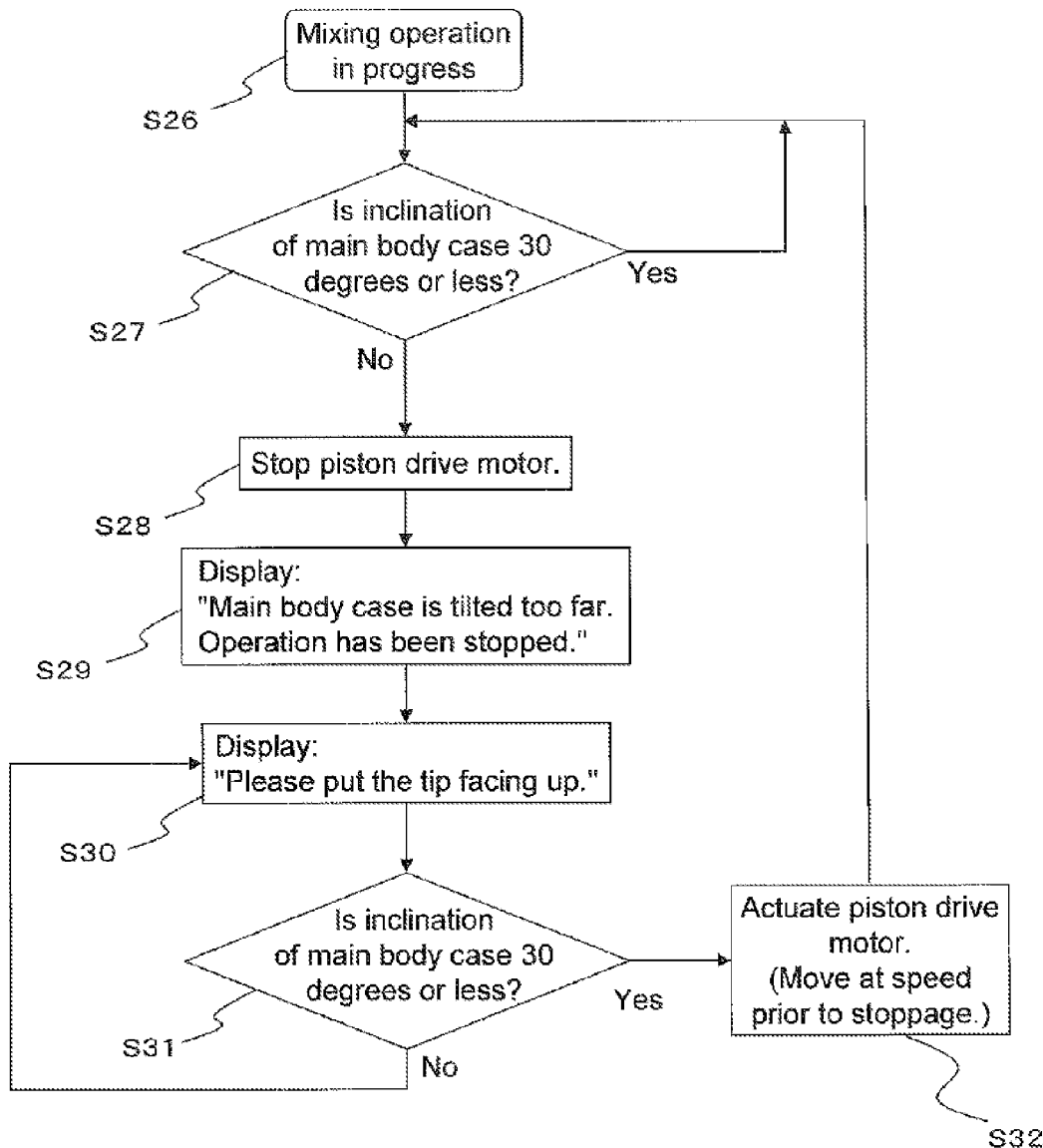
FIG. 7 is a flowchart of the operational control of the pharmaceutical injection device in FIG. 1.

Although not discussed in detail here, the inclination is continuously sensed by the orientation sensor 8 during the operation from S7 onward as shown in FIG. 7 (S26). Here, if the inclination of the main body case 2 exceeds 30 degrees (S27), the piston drive motor 10 is stopped (S28), and the display section 35 gives a warning display of "Main body case is tilted too far. Operation has been stopped" (S29) and "Please put the tip facing up" (S30). This prompts the user not to tilt the main body case 2 more than 30 degrees. S31 is a loop with S30, and is used to check whether the inclination of the main body case 2 has exceeded 30 degrees.

S32 is used to restart the operation prior to the stoppage and return to S8 in the event that it was sensed in S31 that the inclination was 30 degrees or less.

Figure 9B:
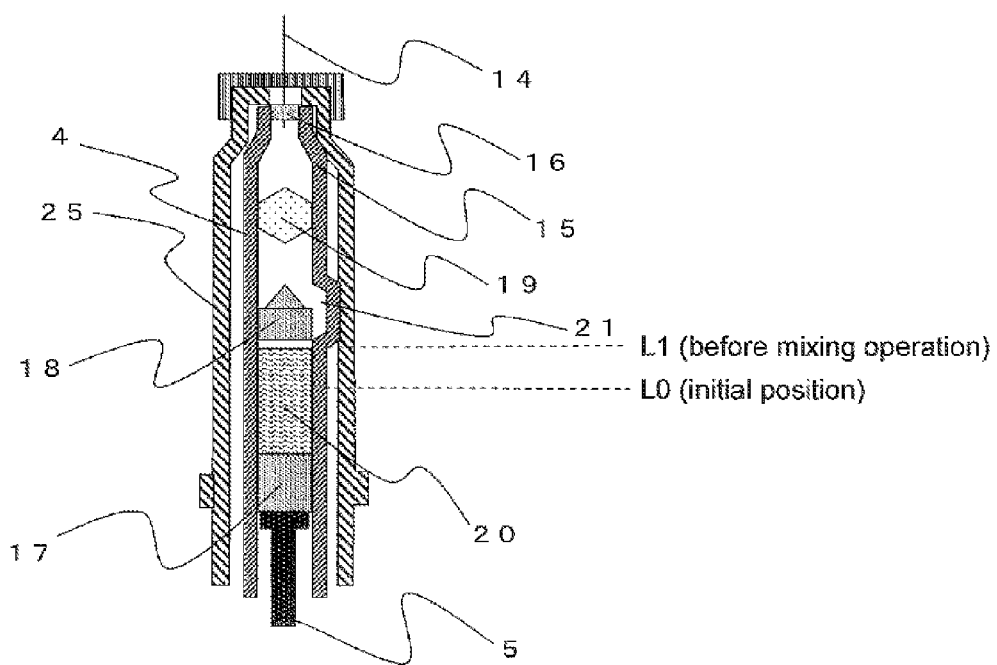
FIG. 9B is a cross section of the operating state during mixing in the pharmaceutical injection device pertaining in FIG. 1.

In S8, as shown FIG. 9A, the piston drive motor 10 is driven from its initial state prior to the mixing operation, at the push-in rate V1. Then, in S9, the movement distance of the piston 5 is calculated by the encoder 26 during drive of the piston 5. Then, in S10, the piston drive motor 10 continues to move at the push-in rate V1 until the rear end of the separation gasket 18 goes from L0 in FIG. 9B (the initial position) to the position L1 a specific distance away. As shown in FIG. 9B, L1 indicates the position where the rear end of the separation gasket 18 touches the bypass 21, and is position information about the movement distance from the initial position L0 to L1, that is, until the rear end of the separation gasket 18 changes from its initial state to a contact state. This movement distance L1 position information is stored ahead of time in the memory 51.

Figure 5:
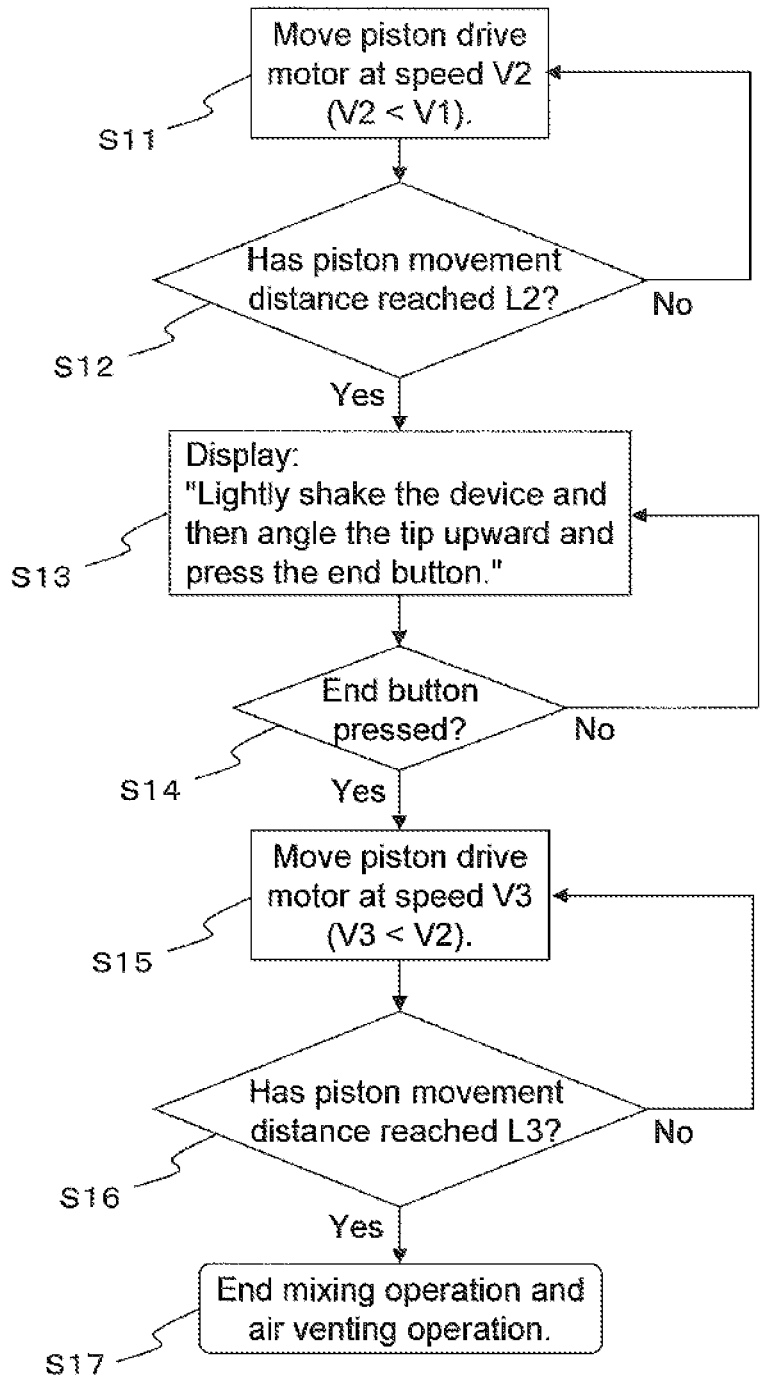
FIG. 5 is a flowchart of the operational control of the pharmaceutical injection device in FIG. 1.

When the rear end of the separation gasket 18 reaches the position L1, the mixing operation commences. As shown in S11 in FIG. 5, the push-in rate V2 of the separation gasket by the piston drive motor 10 is switched so as to be lower than the push-in rate V1 (V2<V1).

Figure 9C:
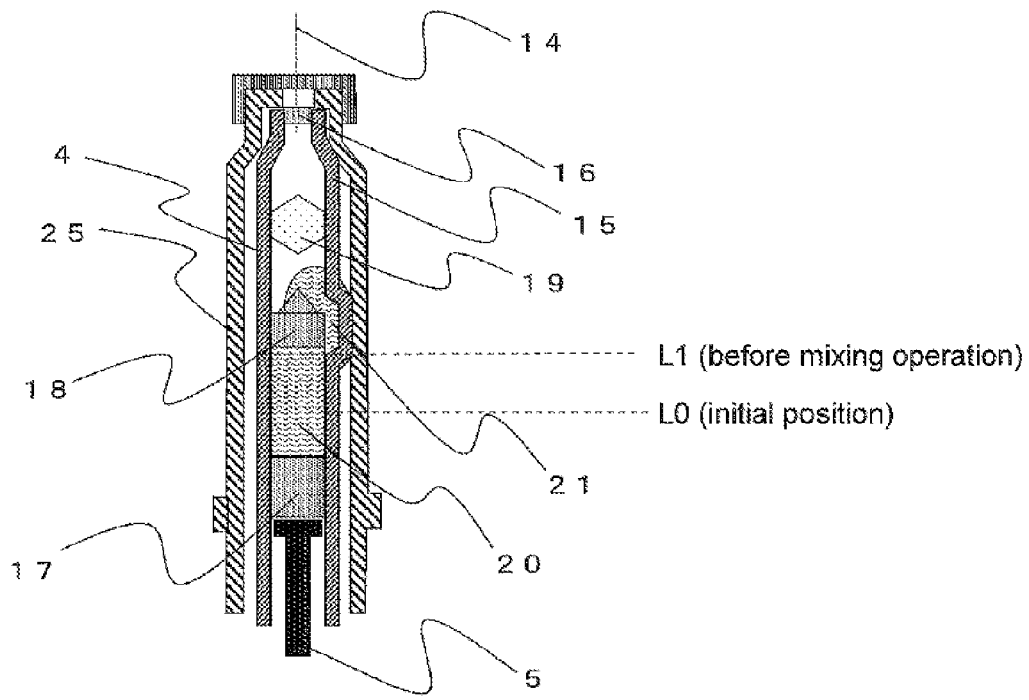
FIG. 9C is a cross section of the operating state during mixing in the pharmaceutical injection device pertaining in FIG. 1.

As shown in FIG. 9C, when the rear end of the separation gasket 18 starts to pass through the bypass 21, the liquid pharmaceutical 20 begins to flow through the bypass 21 to the solid pharmaceutical 19 side.

Figure 9D:
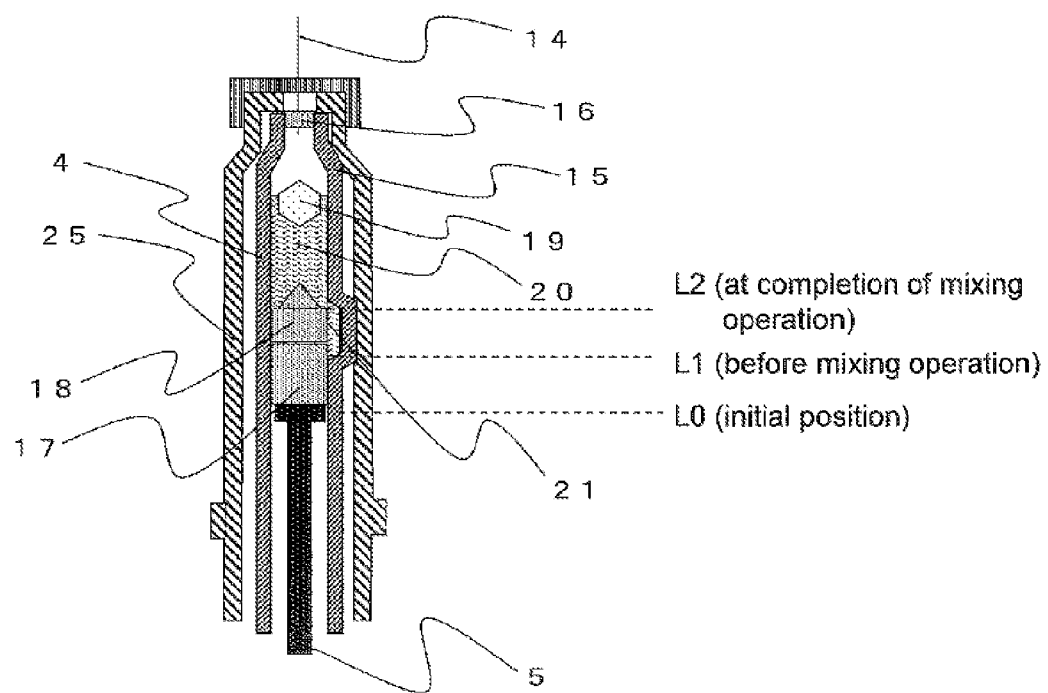
FIG. 9D is a cross section of the operating state during mixing in the pharmaceutical injection device pertaining in FIG. 1.

Then, in S12, the piston drive motor 10 continues to more at the push-in rate V2 until the distal end of the separation gasket 18 reaches the position L2 shown in FIG. 9D. The movement distance from the position L1 to the position L2, as shown in FIG. 9D, is the movement distance up until the separation gasket 18 and the push-in gasket 17 come into contact, that is, it is the movement distance until the separation gasket 18 goes from its initial state to a state of being in contact with the push-in gasket 17. This L2 position information is stored ahead of time in the memory 51.

Because the push-in rate V2 of the separation gasket 18 by the piston drive motor 10 is thus set to be lower than the push-in rate V1, it is less likely that there will be a sudden surge in pressure on the solid pharmaceutical 19 side when the liquid pharmaceutical 20 passes through the bypass 21. As a result, this prevents some of the liquid pharmaceutical from squirting out of the distal end of the injection needle 14 mounted to the distal end gasket 16 of the cylinder 15, or from overflowing more than necessary. That is, liquid leakage from the distal end of the injection needle 14 is also reduced during pharmaceutical mixing, so the mixing operation can be carried out more favorably.

Next, as shown in FIG. 9D, when the distal end position of the separation gasket 18 reaches the position L2, the display section 35 displays "Lightly shake the device and then angle the tip upward and press the end button" as shown in S13, and the operation of the piston drive motor 10 is temporarily halted. Also, the sensing of orientation is not carried out from the time of the above display until the end button 34 is pressed.

Next, in S14, air venting starts when the end button 34 is pressed (see FIG. 1).

In the air venting operation, while the inclination is being sensed by the orientation sensor 8, the push-in rate of the separation gasket 18 by the piston drive motor 10 is switched to a push-in rate V3 so as to be lower than the push-in rate V1 (V3<V1). More preferably, as in this embodiment, the push-in rate V3 is set to be lower than the push-in rate V2 (V3<V2).

In S15, since liquid is most apt to leak from the distal end of the injection needle 14 during the air venting operation, the speed at which the piston 5 is moved is further lowered.

Figure 9E:
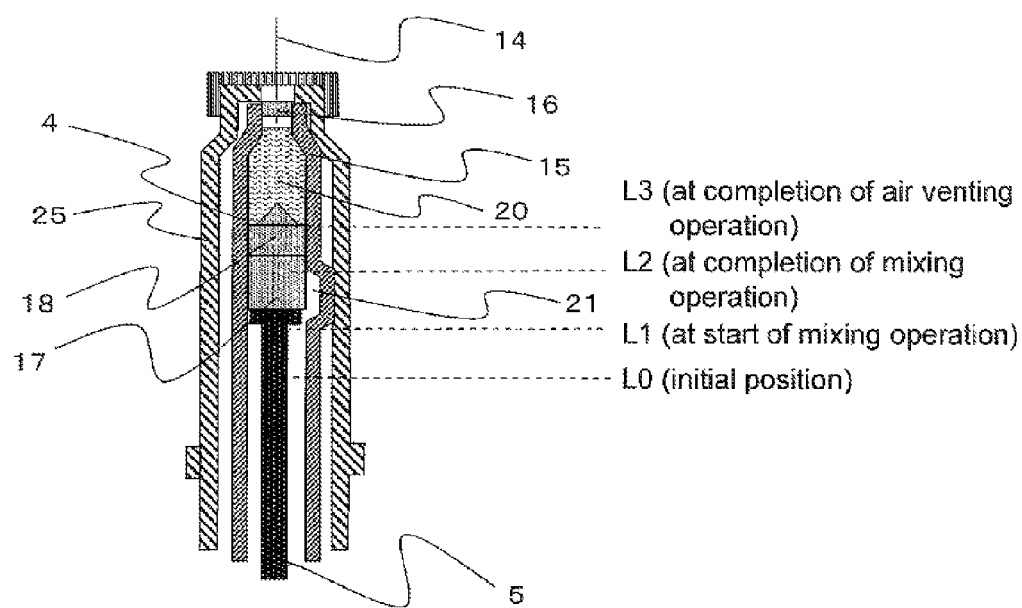
FIG. 9E is a cross section of the operating state during mixing in the pharmaceutical injection device pertaining in FIG. 1.

Then, in S16, the piston drive motor 10 is operated at the push-in rate V3 until the distal end position of the separation gasket 18 arrives at the position L3. As shown in FIG. 9E, the movement distance from the position L2 to the position L3 indicates the position after the separation gasket 18 and the push-in gasket 17 have passed through the bypass 21 in a state of being in contact with each other. Position information about the position L3 is stored ahead of time in the memory 51.

As shown in S17, the air venting operation is ended when the distal end position of the separation gasket 18 reaches the position L3.

Figure 6:
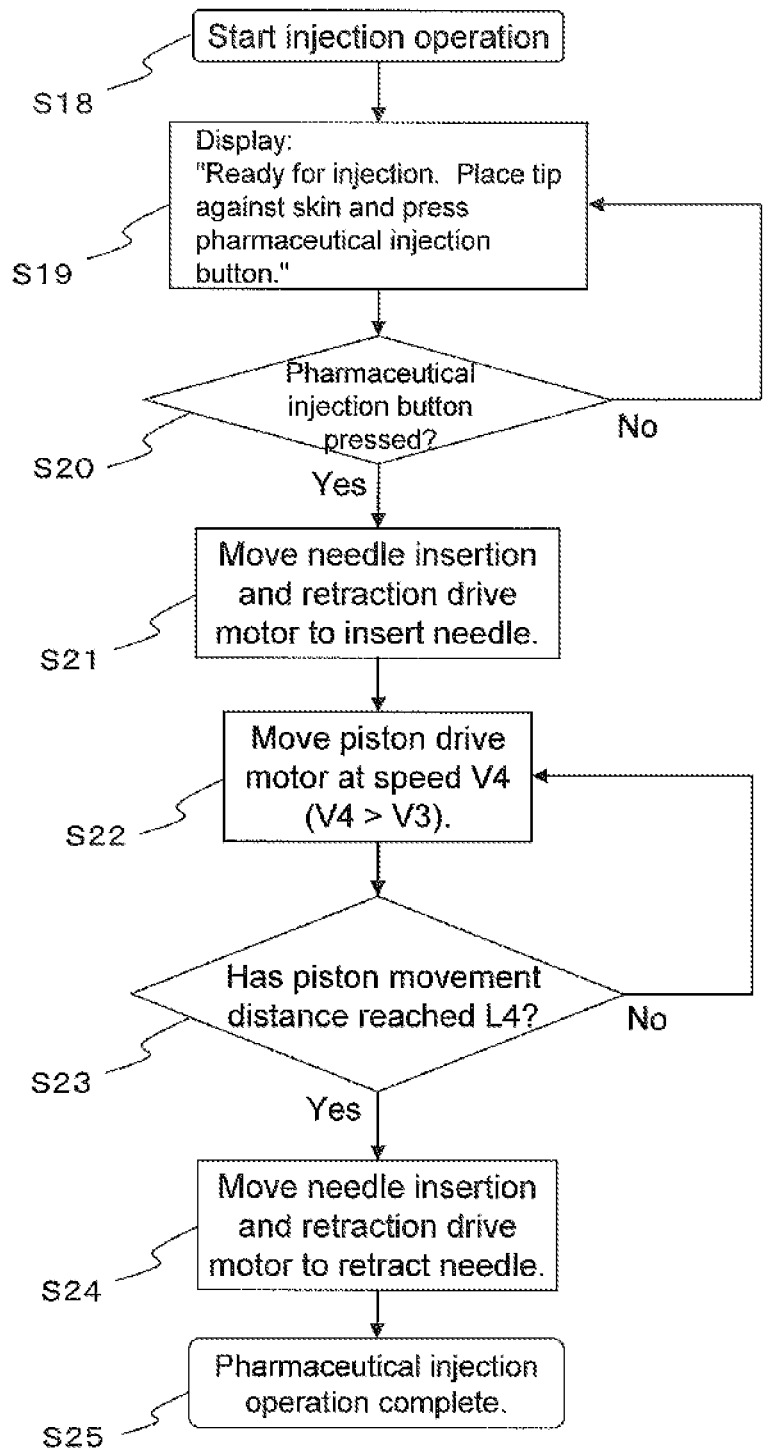
FIG. 6 is a flowchart of the operational control of the pharmaceutical injection device in FIG. 1.

The pharmaceutical injection operation shown in S18 in FIG. 6 is then commenced.

When the automatic mixing and air venting operation discussed above is complete, in S19 the display section 35 display a message of "Ready for injection. Place tip against skin and press pharmaceutical injection button" and the operation of the piston drive motor 10 is temporarily halted.

Next, in S20, the operation of piercing the skin is commenced when the pharmaceutical injection button 33 is pressed.

Next, in S21, the needle insertion and retraction drive motor 12 is driven to perform the needle insertion operation. This "needle insertion operation" refers to an operation of driving the needle insertion and retraction drive motor 12 to move the pharmaceutical syringe mounting portion 3 to the injection needle insertion and retraction opening 1 side, and thereby causing the injection needle 14 to stick out from the injection needle insertion and retraction opening 1.

At this point, since the injection needle insertion and retraction opening 1 is already being pressed against the site on the body where the injection is to be made, the injection needle 14 is moved toward the body and the injection needle 14 is plunged into the body, and the preparatory operation (needle insertion operation) prior to pharmaceutical injection is complete.

Then, in S22, when the preparatory operation (needle insertion operation) prior to pharmaceutical injection is complete, the operation of pharmaceutical injection is commenced.

In the pharmaceutical injection operation, the push-in rate of the separation gasket 18 by the piston drive motor 10 is switched to the push-in rate V4 so as to be higher than the push-in rate V3 (V4>V3).

Since it is unlikely that there will be leakage from the distal end of the injection needle 14 during the pharmaceutical injection operation, the speed at which the piston 5 is moved can be increased.

Then, in S23, the piston drive motor 10 continues to move at the push-in rate V4 until the distal end position of the separation gasket 18 reaches the position L4.

Figure 9F:
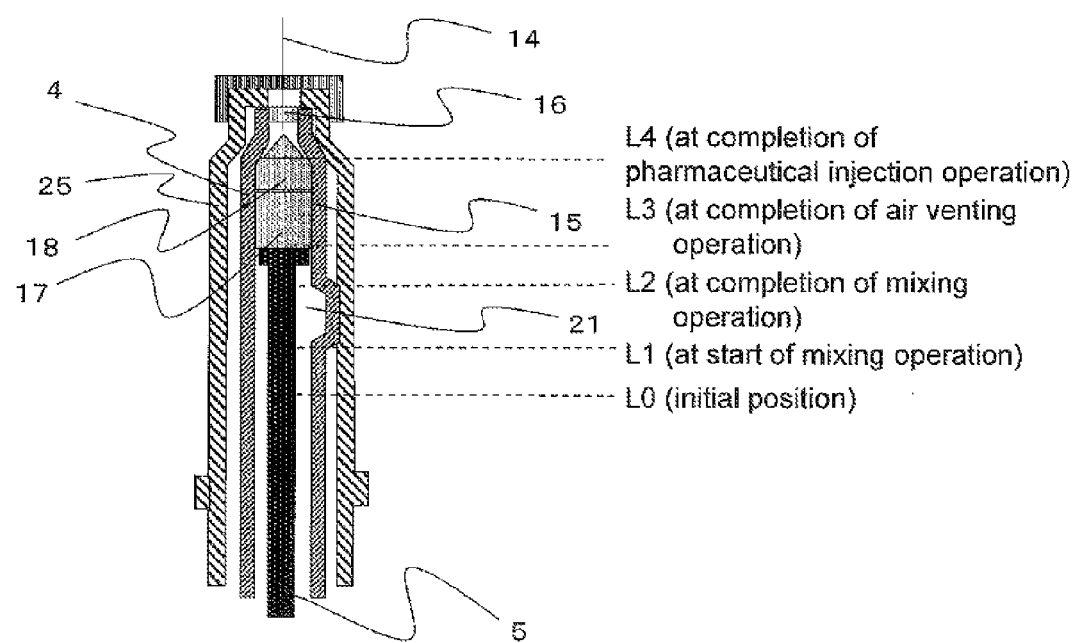
FIG. 9F is a cross section of the operating state during mixing in the pharmaceutical injection device pertaining in FIG. 1.

As shown in FIG. 9F, the movement distance from the position L3 to the position L4 indicates the movement distance up to where the separation gasket 18 reaches the inclined portion of the distal end of the pharmaceutical syringe 4. Position information about this movement distance L4 is stored ahead of time in the memory 51.

Finally, in S24, the needle retraction operation is commenced when the distal end position of the separation gasket 18 reaches the position L4. In the needle retraction operation, the piston drive motor 10 is halted and the needle insertion and retraction drive motor 12 is driven.

This needle retraction operation involves driving the needle insertion and retraction drive motor 12 to move the pharmaceutical syringe mounting portion 3 to the rear end side, and thereby stowing the injection needle 14 inside the injection needle insertion and retraction opening 1.

After this, in S25, when the pharmaceutical syringe mounting portion 3 reaches its initial position prior to the needle insertion operation, the needle retraction operation is complete, and the operation of pharmaceutical injection into the body is ended.

FIG. 8 is a graph of the operating state during mixing with this pharmaceutical injection device. The vertical axis is the applied voltage (value) to a motor driver (not shown) for driving the piston drive motor 10, and the horizontal axis is the rear end position or distal end position of the separation gasket 18, showing a simulation of the flow of the operation at the above-mentioned push-in rates (V1, V2, V3, and V4).

Although not discussed detail here, the push-in rates are determined by changing the voltage values of a piston speed control signal (such as 1.0 volt for V1 and V4, 0.8 volt for V2, and 0.7 volt for V3). It can be seen that as the piston 5 is moved, the push-in rate V2 when the liquid pharmaceutical 20 passes through the bypass 21 is lower than the initial push-in rate V1, the push-in rate V3 during air venting is lower than the push-in rate V2, and the push-in rate V4 during pharmaceutical injection is higher than the push-in rate V3.

The graph in FIG. 8 is just an example, and a waiting period for user manipulation selection can be allocated as needed, such as between V2 and V3, or between V3 and V4. In this case, the mixing operation can be temporarily halted so that the various speeds are all zero. This is generally how the settings are made.

In the above description, position information about L0, L1, L2, L3, and L4 indicated where the distal end position or rear end position of the separation gasket 18 was located within the pharmaceutical syringe 4, but the above-mentioned control may be accomplished with the movement distance of the piston 5 at a separate stage.

As discussed above, the pharmaceutical injection device in this embodiment is such that in the pharmaceutical mixing operation, the push-in rate V2 at the point when the separation gasket 18 passes through the bypass 21 is set lower than the push-in rate V1 when the separation gasket 18 is pushed in until it comes into contact with the bypass 21. Consequently, the liquid pharmaceutical 20 flows gently through the bypass 21 to the solid pharmaceutical 19 side. As a result, leakage from the distal end gasket 16 side can be reduced during this pharmaceutical mixing operation, the surroundings can be kept clean, without the pharmaceutical splashing onto the surrounding area when the pharmaceutical injection device is operated by the user, and the automatic mixing of the pharmaceuticals can be carried out easily and safely.

Next, the most salient features of this embodiment will be described.

Figure 12:
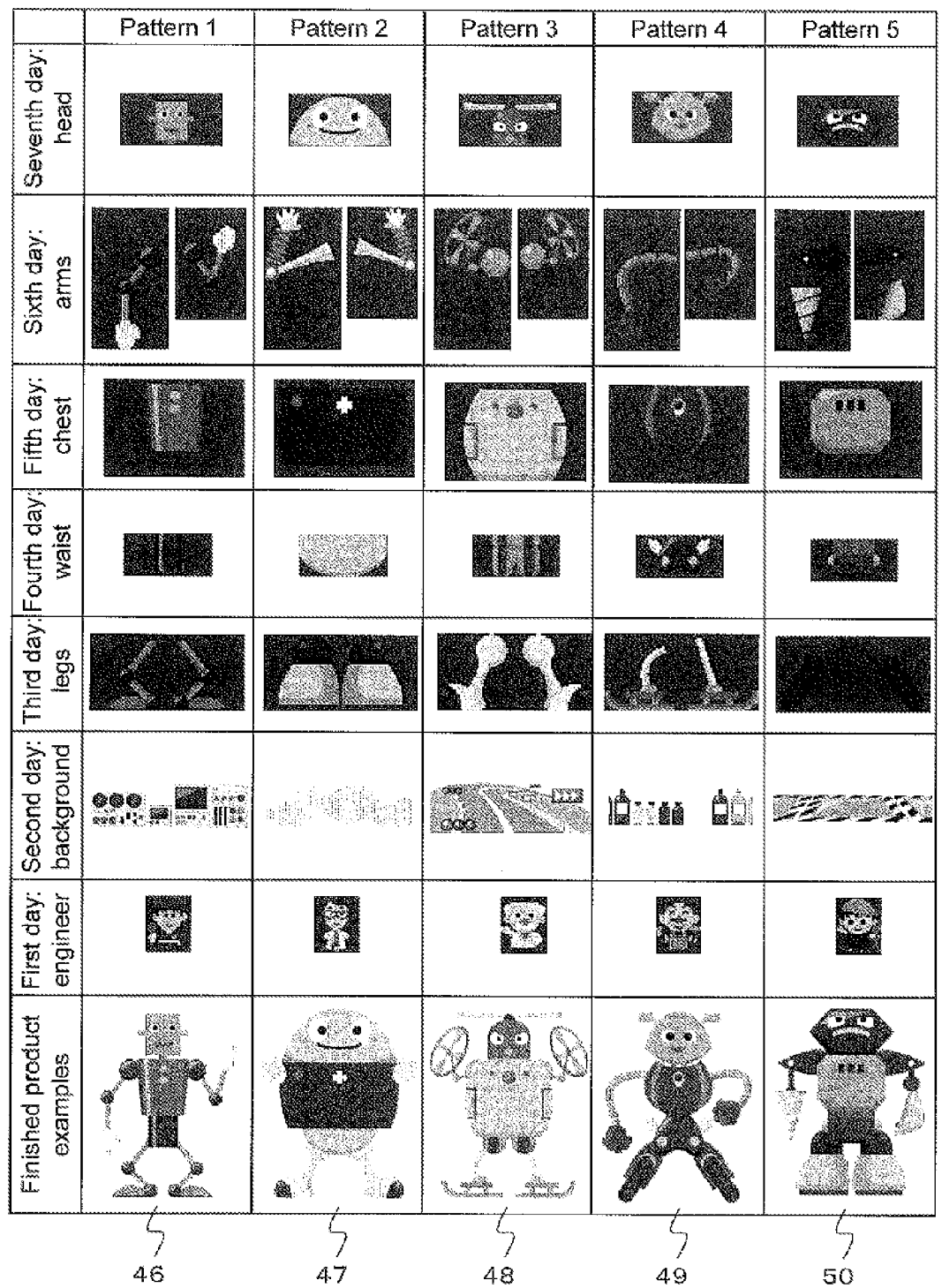
FIG. 12 is a diagram of the operational control of the pharmaceutical injection device in FIG. 1.

A main feature in this embodiment is that the display shown in FIG. 12 is displayed on the display section 35.

In FIG. 12, when pharmaceutical injection is performed properly for seven days, the robots 46 to 50 shown in the bottom row are displayed as a finished product display on the display section 35. In this embodiment, these robots 46 to 50 are chosen from among 78,125 finished products, as will be understood from the following explanation.

With the pharmaceutical injection device in this embodiment, one of the robots 46 to 50, for example, is displayed as a finished product in seven days (one week), on the premise that pharmaceutical injection is performed once a day. First, on the first day, the engineer who will build the robots 46 to 50 is chosen. On the second day, the factory where they will be built is chosen. On the third day, the legs of the robots 46 to 50 are chosen. On the fourth day, the waists of the robots 46 to 50 are chosen. On the fifth day, the chests of the robots 46 to 50 are chosen. On the sixth day, the arms of the robots 46 to 50 are chosen. On the seventh day, the heads of the robots 46 to 50 are chosen, and the display contents chosen on the third to seventh days are combined, so that one of the robots 46 to 50 shown in the bottom row of FIG. 12 is displayed as a finished product on the display section 35.

As can be seen in this example, if there are five patterns put together in seven days, five to the seventh power gives a total of 78,125 possible finished products, so in actual usage, the same robot will never be displayed on the display section 35. Since the engineer and factory on the first and second days are not combined with the robots 46 to 50, they will probably not affect the above-mentioned number of 78,125. In this embodiment, however, the engineer and factory can also affect the robot production by assigning attitudes (thoughts) about robot production to the engineer and the factory. As a result, it is possible to attached the above-mentioned 78,125 finished products.

Figure 10:
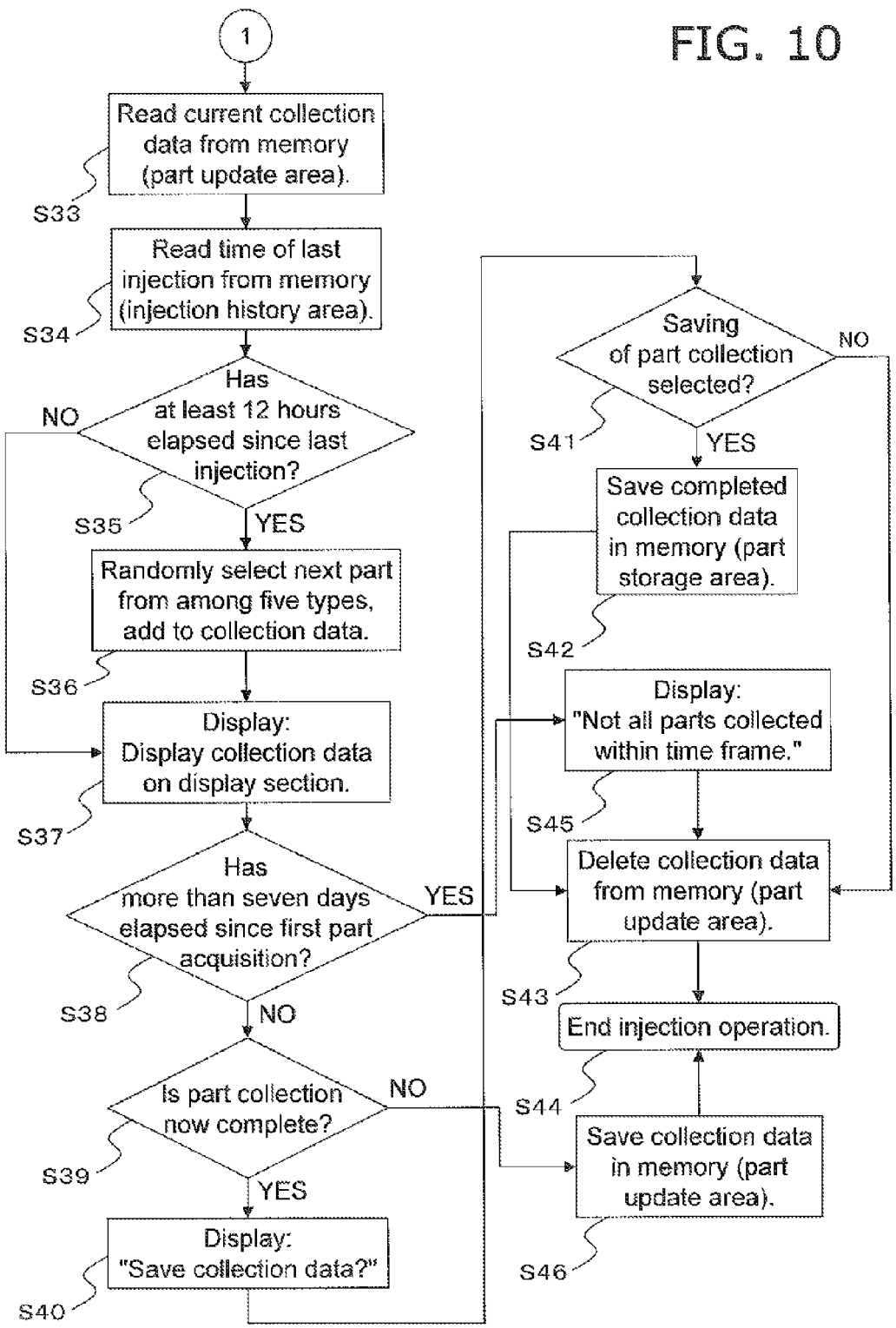
FIG. 10 is a flowchart of the operational control of the pharmaceutical injection device in FIG. 1.
Figure 11:
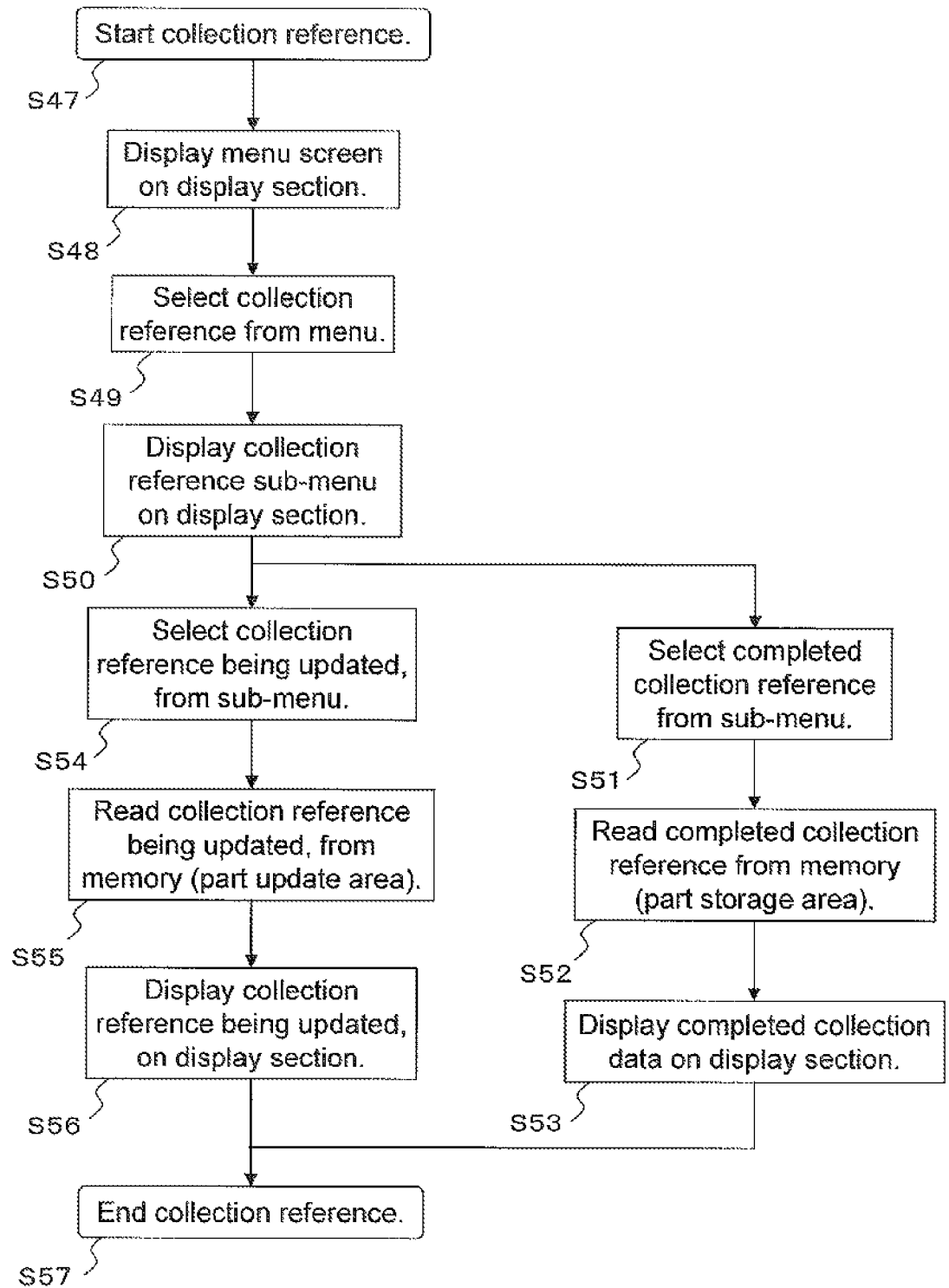
FIG. 11 is a flowchart of the operational control of the pharmaceutical injection device in FIG. 1.

FIGS. 10 and 11 are flowcharts illustrating this display on the display section 35, and the programs thereof are written to the ROM 38 in FIG. 3.

FIG. 10 shows the operation from S25 in FIG. 6, and in S33, collection data from the last time is read from a part update area (not shown) within the memory 51 shown in FIG. 3 (this is one of the parts on the first to seventh days in FIG. 12).

In S34, the last injection time is read from an injection history area (not shown) within the memory 51. In S35, it is determined whether or not the current pharmaceutical injection is at least 12 hours after the last injection time. In S35 here, if at least 12 hours have elapsed since the last injection time, then a part matching the current number of days (the n-th day) shown in FIG. 12 is selected in S36. The selected part is recorded to the part update area (not shown) in the memory 51.

On the other hand, in S35, if at least 12 hours have not elapsed since the last injection time, then the last collection data is displayed on the display section 35. That is, in this embodiment, the pharmaceutical is injected once a day, such as after dinner each day, but if it is anticipated that the pharmaceutical cannot be injected after the next dinner for some reason (such as because the user will be flying), then the user may have to inject the pharmaceutical a little earlier than scheduled. Nevertheless, it is preferable to perform the next pharmaceutical injection if at least 12 hours have elapsed since the last injection time. Thus, in S35, as discussed above, it is determined whether or not at least 12 hours have elapsed since the last injection time. This is also advantageous in a way that will now be described.

Specifically, even if the user should inadvertently perform pharmaceutical injection just to see the robots 46 to 50 shown in FIG. 12, unless at least 12 hours have elapsed since the last pharmaceutical injection, the collection data acquired the last time (data for one of the parts from the first to seventh days in FIG. 12) will merely be displayed again, that is, there will be no update (S37 in FIG. 10). Inadvertent pharmaceutical injection can thus be avoided.

Next, in S38 in FIG. 10, it is determined whether or not it has been more than seven days since the part data displayed on the display section 35 (the part data registered to the part update area in the memory 51) was acquired the first time. If seven days has not been exceeded, in S39 the part data shown in FIG. 12 and collected over the course of seven days is combined, and the robot shown in FIG. 12 (such as one of the robots 46 to 50) is displayed as a finished product on the display section 35 (S40 in FIG. 10). In S40, a display is given that asks the question of whether or not to save the robot displayed on the display section 35 (such as one of the robots 46 to 50).

In S41, a selection is made as to whether or not to leave the robot displayed on the display section 35 (such as one of the robots 46 to 50) as part of a collection. If the selection is to leave the robot, then in S42 the finished product collection data is saved in the part storage area (not shown) of the memory 51. If the selection in S41 was not to leave the robot displayed on the display section 35 (such as one of the robots 46 to 50), then in S43 the finished product collection data is deleted from the part update area of the memory 51.

Also, if the finished product collection data stored in the part storage area (not shown) of the memory 51 is deleted in S42, the flow proceeds to S43.

Then, in S44 the pharmaceutical injection operation is concluded.

Meanwhile, in S38, it is determined that pharmaceutical injection has been properly performed for seven days in a row if it has been more than seven days since the part data displayed on the display section 35 (the part data registered to the part update area of the memory 51) was acquired the first time, and in S45 a display is given on the display section 35 indicating that not all of the parts were collected within the time frame. After this, in S43, the finished product collection data is deleted from the part update area of the memory 51. That is, if pharmaceutical injection has not been properly performed for seven days in a row, the robot shown in FIG. 12 (such as one of the robots 46 to 50) cannot be displayed on the display section 35. Because the user is thus persuaded to avoid this, pharmaceutical injection can be performed properly for seven days in a row and its therapeutic effect enhanced.

In S39, it is determined whether or not the parts collection is complete this time. If seven days' worth of parts have not been collected, in S46 the collection data is saved in the part update area of the memory 51, and in S44 the pharmaceutical injection operation is ended. If the next pharmaceutical injection is then performed, the operation will resume from S33.

FIG. 11 is a flowchart of the flow of operation when the completed collection data collected in the part storage area of the memory 51 (such as the robots 46 to 50 in FIG. 12) is displayed on the display section 35.

That is, in this embodiment, since there are 78,125 possibilities for robots that can be the finished product, what is of interest to the patient is which robots have been collected so far, and this also needs to be displayed sequentially.

First, in S47, the referral to this collection is commenced.

Then, in S48, a menu screen is displayed on the display section 35.

Then, in S49, a collection reference is selected on the menu screen of the display section 35.

Then, in S50, a collection reference sub-menu is displayed on the display section 35, in S51 a completed collection is selected from the sub-menu. Then, in S52 the completed collection data is read from the part storage area in the memory 51, and in S53 the collected robots are sequentially displayed on the display section 35.

Meanwhile, from S50 to S54, if a collection reference that is being updated is selected from the sub-menu, in S55 data that has been collected so far, that is, data from the first to sixth days in FIG. 12, is read from the part update area of the memory 51.

Then, in S56, the part collection is displayed on the display section 35.

S57 is a selection mode when the display of S53 and S56 is ended.

In this embodiment, the operations of performing selection and so forth in FIGS. 10 and 11 were all described in S48, for example, but since a menu screen is displayed on the display section 35, these are executed by selecting options from that menu screen.

Also, in this embodiment, it was described that a plurality of parts are combined according to the results of pharmaceutical injection, and a robot finished product is displayed on a display section, but the present invention is not limited to this.

For example, instead of combining a plurality of parts to complete a robot or other such character, parts may be deleted and taken apart to produce different data patterns, so that the display prompts the user to perform pharmaceutical injection.

INDUSTRIAL APPLICABILITY

With the pharmaceutical injection device of the present invention, even if the user is a child, for example, he can enjoy performing pharmaceutical injection properly as scheduled, which has the effect of enhancing the therapeutic effect, so this device is expected to find widespread acceptance in fields such as pharmaceutical injection devices in which a pharmaceutical mixing operation is required.

REFERENCE SIGNS LIST

1 injection needle insertion and retraction opening
2 main body case
3 pharmaceutical syringe mounting portion
4 pharmaceutical syringe
5 piston
6 drive mechanism
7 controller
7*a* substrate
8 orientation sensor
9 bolt
10 piston drive motor
11 female threads
12 needle insertion and retraction drive motor
13 bolt
14 injection needle
15 cylinder
16 distal end gasket
17 push-in gasket
18 separation gasket
19 solid pharmaceutical
20 liquid pharmaceutical
21 bypass
22 housing
23 distal end cap
24 window
25 cylinder cover
26 encoder
27 control rod
28 distal end cap detector switch
29 control rod
30 syringe cover detector switch
31 power button
32 mix button
33 pharmaceutical injection button
34 end button
35 display section
36 rechargeable battery
37 central processing unit
38 ROM
39 orientation detecting section
39*a* orientation determination section
40 piston movement distance detector
41 motor rotation controller
42 motor drive circuit
43 over-current detection circuit
44 buzzer
45 vibrator
46, 47, 48, 49, 50 robot
51 memory

The invention claimed is:

1. A pharmaceutical injection device, comprising:
a main body case that has an injection needle insertion and retraction opening;
a pharmaceutical syringe mounting portion that is provided within the main body case;
a piston that is provided movably with respect to a pharmaceutical syringe mounted to the pharmaceutical syringe mounting portion;
a drive mechanism configured to drive the piston;
a controller that is electrically connected to the drive mechanism; and
a display section that is electrically connected to the controller,
wherein the controller updates a display content displayed on the display section according to a number of times the drive mechanism has been driven, and saves the updated display content in a memory, so that when the number of times the drive mechanism has been driven reaches a specific number, the display contents during the various instances of drive that were saved in the memory are combined, and when the drive mechanism is driven again within a specific length of time, the controller puts the display content displayed on the display section in a non-updated state.

2. The pharmaceutical injection device according to claim 1, wherein, when the drive mechanism is driven again within a specific length of time, the controller displays the display content from the previous update.

3. The pharmaceutical injection device according claim 1, wherein the controller saves in the memory a finished product display obtained by combining the display contents for the various instances of drive.

4. The pharmaceutical injection device according to claim 3, wherein the controller selectively displays the finished product display saved in the memory, and the display content from the last update.

5. A pharmaceutical injection device, comprising:

a main body case that has an injection needle insertion and retraction opening;

a pharmaceutical syringe mounting portion that is provided within the main body case;

a piston that is provided movably with respect to a pharmaceutical syringe mounted to the pharmaceutical syringe mounting portion;

a drive mechanism configured to drive the piston;

a controller that is electrically connected to the drive mechanism; and a display section that is electrically connected to the controller, wherein the controller updates a display content displayed on the display section according to a number of times the drive mechanism has been driven, and saves the updated display content in a memory, so that when the number of times the drive mechanism has been driven reaches a specific number, the display contents during the various instances of drive that were saved in the memory are combined, and when the number of times the drive mechanism has been driven within a specific length of time does not reach a specific number, the controller causes the display section to display a message to the effect that a finished product display in which the display contents for the various instances of drive are combined cannot be given.

6. The pharmaceutical injection device according to claim 5, wherein, when the number of times the drive mechanism has been driven within a specific length of time does not reach a specific number, the controller deletes the display content saved in the memory.

7. The pharmaceutical injection device according claim 5, wherein the controller saves in the memory a finished product display obtained by combining the display contents for the various instances of drive.

8. The pharmaceutical injection device according to claim 7, wherein the controller selectively displays the finished product display saved in the memory, and the display content from the last update.

* * * * *